United States Patent
Cully et al.

(10) Patent No.: US 10,842,918 B2
(45) Date of Patent: Nov. 24, 2020

(54) LENGTH EXTENSIBLE IMPLANTABLE DEVICE AND METHODS FOR MAKING SUCH DEVICES

(71) Applicant: W. L. Gore & Associates, Inc., Newark, DE (US)

(72) Inventors: Edward H. Cully, Flagstaff, AZ (US); Jeffrey B. Duncan, Flagstaff, AZ (US)

(73) Assignee: W.L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 14/558,296

(22) Filed: Dec. 2, 2014

(65) Prior Publication Data

US 2015/0157770 A1  Jun. 11, 2015

Related U.S. Application Data

(60) Provisional application No. 61/912,414, filed on Dec. 5, 2013.

(51) Int. Cl.
| | | |
|---|---|---|
| *A61F 2/06* | (2013.01) | |
| *A61F 2/07* | (2013.01) | |
| *A61F 2/82* | (2013.01) | |
| *B32B 37/12* | (2006.01) | |
| *B32B 37/14* | (2006.01) | |
| (Continued) | | |

(52) U.S. Cl.
CPC ............ *A61L 31/146* (2013.01); *A61F 2/06* (2013.01); *A61F 2/07* (2013.01); *A61F 2/82* (2013.01); *B29D 23/001* (2013.01); *B32B 37/12* (2013.01); *B32B 37/142* (2013.01); *B32B 38/0012* (2013.01); *A61F 2210/0071* (2013.01); *A61F 2220/005* (2013.01); *A61F 2240/001* (2013.01); *A61F 2250/0028* (2013.01); *A61F 2250/0037* (2013.01); *A61F 2250/0048* (2013.01); *B29K 2027/18* (2013.01)

(58) Field of Classification Search
CPC ............... A51F 2250/0007; B32B 7/12; A61F 2250/0007
USPC ................................................. 623/1.44, 1.39
See application file for complete search history.

(56) References Cited

U.S. PATENT DOCUMENTS

| | | |
|---|---|---|
| 3,953,566 A | 4/1976 | Gore |
| 4,187,390 A | 2/1980 | Gore |
| (Continued) | | |

FOREIGN PATENT DOCUMENTS

| | | |
|---|---|---|
| CA | 2462509 A1 | 4/2003 |
| CN | 101926699 A | 12/2010 |
| (Continued) | | |

OTHER PUBLICATIONS

International Search Report and Written Opinion for PCT/US2014/068430 dated Feb. 20, 2015, corresponding to U.S. Appl. No. 14/558,296, 4 pages.

(Continued)

*Primary Examiner* — Jacqueline Woznicki

(57) ABSTRACT

A length extensible implantable device includes a porous member and a longitudinal constraining member. The longitudinal constraining member can constrain at least a portion, up to the entire length of, the porous member in the longitudinal direction. The length of the longitudinally constrained portion can be expanded by applying force to the porous member. The porous member may be a porous tubular member.

23 Claims, 4 Drawing Sheets

(51) Int. Cl.
*A61L 31/14* (2006.01)
*B29D 23/00* (2006.01)
*B32B 38/00* (2006.01)
*B29K 27/18* (2006.01)

(56) References Cited

U.S. PATENT DOCUMENTS

| | | |
|---|---|---|
| 4,332,035 A | 6/1982 | Mano |
| 4,877,661 A | 10/1989 | House et al. |
| 4,955,899 A | 9/1990 | Della Corna et al. |
| 5,026,513 A | 6/1991 | House et al. |
| 5,071,609 A | 12/1991 | Tu et al. |
| 5,476,589 A | 12/1995 | Bacino |
| 5,534,007 A | 7/1996 | St. Germain et al. |
| 5,549,663 A | 8/1996 | Cottone et al. |
| 5,673,102 A | 9/1997 | Suzuki et al. |
| 5,708,044 A | 1/1998 | Branca |
| 5,718,973 A | 2/1998 | Lewis et al. |
| 5,752,934 A | 5/1998 | Campbell et al. |
| 5,759,192 A | 6/1998 | Saunders |
| 5,769,884 A | 6/1998 | Solovay |
| 5,772,884 A | 6/1998 | Tanaka et al. |
| 5,788,626 A * | 8/1998 | Thompson ............... A61L 31/10 623/1.15 |
| 5,814,405 A | 9/1998 | Branca et al. |
| 5,824,043 A | 10/1998 | Cottone, Jr. |
| 5,843,158 A | 12/1998 | Lenker et al. |
| 5,843,161 A | 12/1998 | Solovay |
| 5,843,171 A | 12/1998 | Campbell et al. |
| 5,853,419 A | 12/1998 | Imran |
| 5,925,061 A | 7/1999 | Ogi et al. |
| 5,935,162 A | 8/1999 | Dang |
| 6,010,529 A | 1/2000 | Herweck et al. |
| 6,013,854 A | 1/2000 | Moriuchi |
| 6,042,588 A | 3/2000 | Munsinger et al. |
| 6,042,605 A | 3/2000 | Martin et al. |
| 6,042,606 A | 3/2000 | Frantzen |
| 6,174,329 B1 | 1/2001 | Callol et al. |
| 6,190,406 B1 | 2/2001 | Duerig et al. |
| 6,217,609 B1 | 4/2001 | Haverkost |
| 6,245,012 B1 | 6/2001 | Kleshinski |
| 6,261,320 B1 | 7/2001 | Tam et al. |
| 6,261,620 B1 | 7/2001 | Leadbeater |
| 6,336,937 B1 | 1/2002 | Vonesh et al. |
| 6,352,552 B1 | 3/2002 | Levinson et al. |
| 6,379,382 B1 | 4/2002 | Yang |
| 6,436,132 B1 | 8/2002 | Patel et al. |
| 6,488,701 B1 | 12/2002 | Nolting et al. |
| 6,541,589 B1 | 4/2003 | Baillie |
| 6,620,190 B1 | 9/2003 | Colone |
| 6,626,939 B1 | 9/2003 | Burnside et al. |
| 6,673,102 B1 * | 1/2004 | Vonesh ............... A61F 2/07 623/1.11 |
| 6,673,107 B1 | 1/2004 | Brandt et al. |
| 6,730,120 B2 | 5/2004 | Berg et al. |
| 6,755,856 B2 | 6/2004 | Fierens et al. |
| 6,758,858 B2 | 7/2004 | McCrea et al. |
| 6,890,350 B1 | 5/2005 | Walak |
| 7,022,132 B2 * | 4/2006 | Kocur ............... A61F 2/90 623/1.11 |
| 7,049,380 B1 | 5/2006 | Chang et al. |
| 7,083,642 B2 | 8/2006 | Sirhan et al. |
| 7,105,018 B1 | 9/2006 | Yip et al. |
| 7,306,729 B2 | 12/2007 | Bacino et al. |
| 7,419,678 B2 | 9/2008 | Falotico |
| 7,531,611 B2 | 5/2009 | Sabol et al. |
| 7,789,908 B2 | 9/2010 | Sowinski et al. |
| 7,811,314 B2 | 10/2010 | Fierens et al. |
| 7,815,763 B2 | 10/2010 | Fierens et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 8,585,753 B2 | 11/2013 | Scanlon et al. |
| 9,345,601 B2 | 5/2016 | Jantzen et al. |
| 9,737,422 B2 | 8/2017 | Armstrong et al. |
| 9,795,496 B2 | 10/2017 | Armstrong et al. |
| 9,839,540 B2 | 12/2017 | Armstrong et al. |
| 9,931,193 B2 | 4/2018 | Cully et al. |
| 10,166,128 B2 | 1/2019 | Armstrong et al. |
| 10,279,084 B2 | 5/2019 | Goepfrich et al. |
| 10,335,298 B2 | 7/2019 | Armstrong et al. |
| 10,507,124 B2 | 12/2019 | Armstrong et al. |
| 2001/0053929 A1 | 12/2001 | Vonesh et al. |
| 2002/0076542 A1 | 6/2002 | Kramer et al. |
| 2002/0198588 A1 * | 12/2002 | Armstrong ............... A61F 2/07 623/1.13 |
| 2003/0055494 A1 | 3/2003 | Bezuidenhout et al. |
| 2003/0060871 A1 | 3/2003 | Hill et al. |
| 2003/0180488 A1 | 9/2003 | Lim et al. |
| 2004/0024442 A1 | 2/2004 | Sowinski et al. |
| 2004/0024448 A1 | 2/2004 | Chang et al. |
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0224442 A1 | 11/2004 | Grigg |
| 2004/0260277 A1 | 12/2004 | Maguire |
| 2005/0080476 A1 | 4/2005 | Gunderson et al. |
| 2005/0137680 A1 | 6/2005 | Ortiz et al. |
| 2005/0283224 A1 | 12/2005 | King |
| 2006/0009835 A1 | 1/2006 | Osborne et al. |
| 2006/0015171 A1 * | 1/2006 | Armstrong ....... A61B 17/12022 623/1.12 |
| 2006/0036311 A1 | 2/2006 | Nakayama et al. |
| 2006/0106337 A1 | 5/2006 | Blankenship |
| 2006/0118236 A1 * | 6/2006 | House ............... A61L 27/16 156/294 |
| 2006/0135985 A1 | 6/2006 | Cox et al. |
| 2006/0161241 A1 | 7/2006 | Barbut et al. |
| 2006/0190070 A1 * | 8/2006 | Dieck ............... A61F 2/90 623/1.12 |
| 2006/0259133 A1 | 11/2006 | Sowinski et al. |
| 2006/0271091 A1 | 11/2006 | Campbell et al. |
| 2006/0276883 A1 | 12/2006 | Greenberg et al. |
| 2007/0012624 A1 | 1/2007 | Bacino et al. |
| 2007/0060999 A1 | 3/2007 | Randall et al. |
| 2007/0129786 A1 | 6/2007 | Beach et al. |
| 2007/0207186 A1 | 9/2007 | Scanlon et al. |
| 2007/0207816 A1 | 9/2007 | Spain |
| 2007/0208421 A1 | 9/2007 | Quigley |
| 2007/0213800 A1 | 9/2007 | Fierens et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0051876 A1 | 2/2008 | Ta et al. |
| 2008/0097301 A1 | 4/2008 | Alpini et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0036954 A1 | 2/2009 | Beach et al. |
| 2009/0043373 A1 | 2/2009 | Arnault De La Menardiere et al. |
| 2009/0104247 A1 | 4/2009 | Pacetti |
| 2009/0182413 A1 | 7/2009 | Burkart et al. |
| 2009/0306766 A1 | 12/2009 | McDermott et al. |
| 2010/0016940 A1 | 1/2010 | Shokoohi et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0159171 A1 | 6/2010 | Clough |
| 2010/0256738 A1 | 10/2010 | Berglund |
| 2010/0286760 A1 | 11/2010 | Beach et al. |
| 2010/0305682 A1 | 12/2010 | Furst |
| 2011/0009953 A1 | 1/2011 | Luk et al. |
| 2011/0087318 A1 | 4/2011 | Daugherty et al. |
| 2012/0323211 A1 | 12/2012 | Ogle et al. |
| 2013/0131780 A1 | 5/2013 | Armstrong et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |

(56) References Cited

U.S. PATENT DOCUMENTS

| | | |
|---|---|---|
| 2013/0253466 A1 | 9/2013 | Campbell et al. |
| 2013/0297003 A1 | 11/2013 | Pinchuk |
| 2014/0135897 A1 | 5/2014 | Cully et al. |
| 2014/0172066 A1 | 6/2014 | Goepfrich et al. |
| 2014/0180402 A1 | 6/2014 | Bruchman et al. |
| 2015/0005870 A1 | 1/2015 | Kovach et al. |
| 2015/0313871 A1 | 11/2015 | Li et al. |
| 2016/0015422 A1 | 1/2016 | De Cicco et al. |
| 2017/0065400 A1 | 3/2017 | Armstrong et al. |
| 2017/0216062 A1 | 8/2017 | Armstrong et al. |
| 2018/0177583 A1 | 6/2018 | Cully et al. |
| 2019/0125517 A1 | 5/2019 | Cully et al. |
| 2019/0209739 A1 | 7/2019 | Goepfrich et al. |
| 2019/0216592 A1 | 7/2019 | Cully et al. |

FOREIGN PATENT DOCUMENTS

| | | |
|---|---|---|
| EP | 0293090 A2 | 11/1988 |
| EP | 0313263 A2 | 4/1989 |
| EP | 0 775 472 | 5/1997 |
| EP | 0815806 A2 | 1/1998 |
| EP | 0893108 A2 | 1/1999 |
| EP | 1666003 A1 | 6/2006 |
| EP | 2255750 A2 | 12/2010 |
| JP | 02-000645 A | 1/1990 |
| JP | H09241412 A | 9/1997 |
| JP | H11290448 A | 10/1999 |
| JP | 11-512635 A | 11/1999 |
| JP | 2001509702 A | 7/2001 |
| JP | 2007-526098 A | 9/2007 |
| JP | 2008-506459 A | 3/2008 |
| JP | 2010-500107 A | 1/2010 |
| JP | 2010504174 A | 2/2010 |
| JP | 2010535075 A1 | 11/2010 |
| RU | 2124986 C1 | 1/1999 |
| WO | 94/13224 A1 | 6/1994 |
| WO | WO9416802 A1 | 8/1994 |
| WO | WO9505555 A1 | 2/1995 |
| WO | 96/07370 | 3/1996 |
| WO | 1996040348 A1 | 12/1996 |
| WO | WO9710871 A1 | 3/1997 |
| WO | 1999026558 A1 | 6/1999 |
| WO | WO0041649 A1 | 7/2000 |
| WO | WO0047271 A1 | 8/2000 |
| WO | 01/64278 A1 | 9/2001 |
| WO | WO0174272 A2 | 10/2001 |
| WO | WO02060506 A1 | 8/2002 |
| WO | 2003003946 A1 | 1/2003 |
| WO | 2004000375 A1 | 12/2003 |
| WO | 2006019626 A2 | 2/2006 |
| WO | 2006058322 A2 | 6/2006 |
| WO | 2008021002 A1 | 2/2008 |
| WO | 2008028964 A2 | 3/2008 |
| WO | 2008036870 A2 | 3/2008 |
| WO | 2008049045 A2 | 4/2008 |
| WO | 2008/097589 A1 | 8/2008 |
| WO | 2009017827 A1 | 2/2009 |
| WO | 2009100210 A1 | 8/2009 |
| WO | 2009108355 A1 | 9/2009 |
| WO | 2010006783 A1 | 1/2010 |
| WO | 2010008570 A1 | 1/2010 |
| WO | 2010030766 A1 | 3/2010 |
| WO | 2010132707 A1 | 11/2010 |
| WO | 2010150208 A2 | 12/2010 |
| WO | 2011098565 A1 | 8/2011 |
| WO | 2012/011261 A1 | 1/2012 |
| WO | 2012099979 A1 | 7/2012 |
| WO | 2012/158944 A1 | 11/2012 |
| WO | 2013/074663 A2 | 5/2013 |
| WO | 2013109337 A1 | 7/2013 |

OTHER PUBLICATIONS

International Search Report and Written Opinion issued in PCT/US2011/061165, dated Oct. 1, 2012, 20 pages.

International Search Report and Written Opinion issued in PCT/US2012/066518, dated Feb. 4, 2013, 10 pages.

International Search Report issued in PCT/US2014/013496, dated Dec. 2, 2014, 3 pages.

Nakayama, Yasuhide. Microporous Stent Achieves Brain Aneurysm Occlusion Without Disturbing Branching Flow. NeuroNews Nov. 2012; 8:1-2.

Nishi S, Nakayama Y, Ishibashi-Ueda H, Okamoto Y, Yoshida M. Development of microporous self-expanding stent grafts for treating cerebral aneurysms: designing micropores to control intimal hyperplasia. J Artif Organs 2011; 14:348-356.

International Preliminary Report on Patentability issued in PCT/US2016/028671, dated Nov. 1, 2018, 12 pages.

European Search Report and Search Opinion Received for EP Application No. 16899644.5, dated Oct. 30, 2019, 8 pages.

European Search Report and Search Opinion Received for EP Application No. 18167101, dated Jul. 25, 2018, 9 pages.

European Search Report from EP16196687.4, dated Nov. 21, 2017, 5 pages.

Extended European Search Report issued in EP Application No. 17186750.0, dated Oct. 24, 2017, 7 pages.

International Preliminary Report on Patentability received for PCT Patent Application No. PCT/US11/61165, dated Jul. 25, 2013, 14 pages.

International Preliminary Report on Patentability received for PCT Patent Application No. PCT/US12/65066, dated May 30, 2014, 14 pages.

International Preliminary Report on Patentability received for PCT Patent Application No. PCT/US14/68430, dated Jun. 16, 2016, 8 pages.

International Preliminary Report on Patentability received for PCT Patent Application No. PCT/US2013/076405, dated Jul. 2, 2015, 10 pages.

International Preliminary Report on Patentability received for PCT Patent Application No. PCT/US2014/013496, dated Aug. 11, 2016, 7 pages.

International Search Report and Written Opinion issued in PCT/US2012/064908, dated Feb. 4, 2013, 10 pages.

International Search Report and Written Opinion issued in PCT/US2012065066, dated Nov. 11, 2013, 9 pages.

International Search Report and Written Opinion issued in PCT/US2016/028671, dated Jul. 28, 2016, 19 pages.

International Search Report for PCT/US2014/013496 dated Dec. 2, 2014, corresponding to U.S. Appl. No. 13/755,481, 4 pages.

International Search Report issued in PCT/US2013/076405, dated May 6, 2014, 7 pages.

International Written Opinion received for PCT Patent Application No. PCT/US2014/013496, dated Dec. 2, 2014, 5 pages.

Partial International Search Report for PCT/US2012/065066, dated Jul. 1, 2013, corresponding to U.S. Appl. No. 13/675,959, 3 pages.

\* cited by examiner

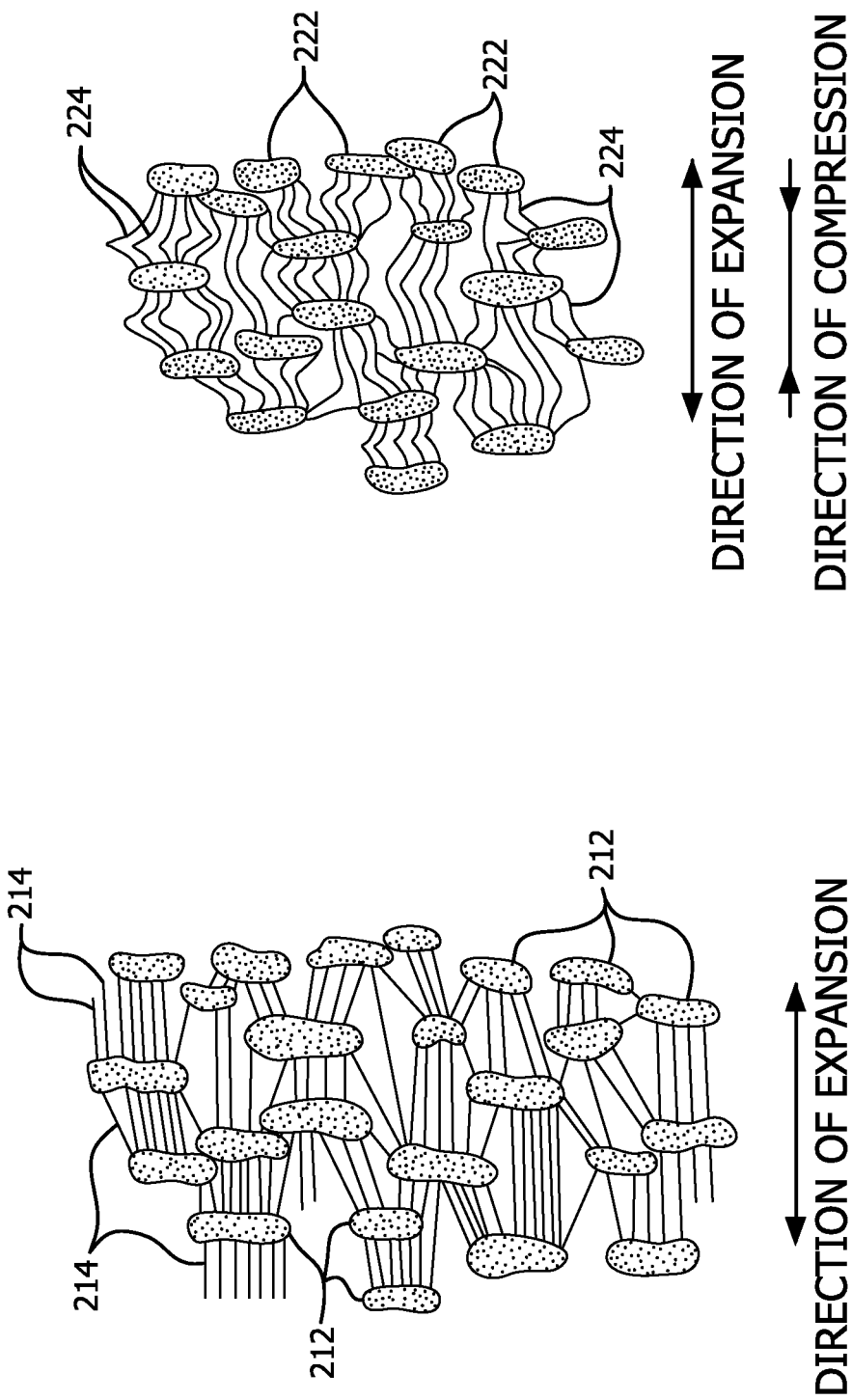

LENGTH EXTENSIBLE IMPLANTABLE DEVICE AND METHODS FOR MAKING SUCH DEVICES

TECHNICAL FIELD

This disclosure relates to length extensible implantable devices and methods for making such devices that may be used for providing a lumen for fluid flow in bodily cavities, organs, and vessels within a patient.

BACKGROUND

Medical devices are frequently used to treat the anatomy of patients. Such devices can be permanently or semi-permanently implanted in the anatomy to provide treatment to a patient. Frequently, these devices, including stents, grafts, stent-grafts, filters, valves, occluders, markers, mapping devices, therapeutic agent delivery devices, prostheses, pumps, bandages, and other endoluminal and implantable devices, are inserted into the body at an insertion point and delivered to a treatment site using a catheter.

Implantable devices such as grafts and stent-grafts are used in a variety of places in the human body to repair, support, and/or replace anatomical lumens, such as blood vessels, respiratory ducts, gastrointestinal ducts, and the like. Such devices can, for example, provide lumens for blood flow. In such configurations, flexible and durable devices are needed.

The selection of such implantable devices can pose potential issues. For example, the particularities of the anatomy of one patient may require a device having a different length than a device suitable for another patient. As a result, it may be difficult to determine the necessary size of a device, and, in many instances, the desired device size may be difficult to obtain.

As such, there is an ongoing need to provide devices, such as grafts and/or stent-grafts, which have adjustable length properties to provide a range of available lengths. Such devices may improve the ability of a treatment provider to properly size a device for the anatomy of a patient.

SUMMARY

In a first general aspect, a length extensible implantable device for supporting, repairing, and/or replacing a lumen in the body of a patient includes a porous tubular member capable of being extended to a desired length. The porous tubular member comprises a longitudinally compressed portion covered and maintained in the compressed configuration by a longitudinal constraining member. The longitudinal constraining member can comprise a film wrap or a perforated tube, among other structures.

In various implementations, a length extensible implantable device is formed by longitudinally compressing a porous tubular member, surrounding a portion of the tubular member with a longitudinal constraining member, and releasing the compressive force. In such implementations, the longitudinally constraining member constrains the portion of the tubular member in the longitudinally compressed configuration. The longitudinal constraining member can optionally be secured to the portion of the porous tubular member by, for example, an adhesive. More than one longitudinal constraining member can used. Further, more than one portion of the porous tubular member can be surrounded by one or more longitudinal constraining members.

The details of one or more embodiments are set forth in the accompanying drawings and the description below. Other features, objects, and advantages will be apparent from the description and the drawings, and from the claims.

BRIEF DESCRIPTION OF THE DRAWINGS

FIGS. 2A and 2B are schematic representations of a microstructure of ePTFE material of the prior art;

Like reference symbols in the various drawings indicate like elements.

DETAILED DESCRIPTION OF THE DRAWINGS

This disclosure describes devices, systems, and methods that are useful, for example, for repairing, supporting, and/or replacing anatomical lumens. Several implantable medical devices are described herein, and in general any of the features described with respect to a particular device may also be used with any of the other devices described herein. In some examples, one or more features described with respect to a particular device may be added to or included with another device. Also, various combinations or sub-combinations of any of the features described herein may generally be used with any of the devices described herein.

In general, any of the implantable devices described herein can be delivered to, and deployed at, an in vivo deployment site within a body of a patient using variously minimally invasive surgical techniques. Likewise, these devices may also be surgically implanted via vascular surgical techniques.

Further, any of the implantable medical devices described herein can be delivered to, and deployed at, an in vivo deployment site within a body of a patient using various minimally invasive transcatheter deployment techniques. For example, any of the implantable medical devices described herein may be releasably attached to a delivery catheter, and the device and delivery catheter may be loaded into a delivery sheath. The delivery sheath may be introduced to the vasculature of the patient and advanced through the vasculature, until a distal end of the delivery sheath is located at or near the target in vivo deployment site. The implantable medical device may be deployed at the deployment site, for example, by retracting the delivery sheath and/or advancing the delivery catheter and the implantable medical device and detaching the implantable medical device from the delivery catheter. The delivery catheter and delivery sheath can then be withdrawn or retracted from the body of the patient.

Any of the implantable medical devices discussed herein can be used to repair, replace, and/or provide support to a body lumen. In various embodiments, implantable medical devices of the present disclosure can be used in a body lumen, including those within the circulatory and gastrointestinal systems.

As used herein, "implantable" means implanted in the body of a patient for more than 29 days.

As used herein, the term "constrain" means: (i) to limit extension, occurring either through self-expansion or assisted expansion, of the length of an implantable device; or (ii) to cover or surround, but not otherwise restrain, an implantable device such as for storage or biocompatibility reasons and/or to provide protection to the implantable device and/or the vasculature.

Figure 1A:
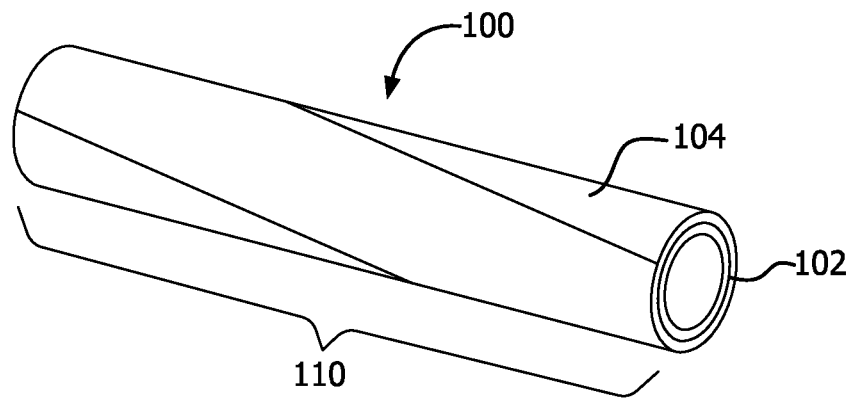
FIGS. 1A-1C are perspective views of various length extensible implantable devices in accordance with the present disclosure.
Figure 1B:
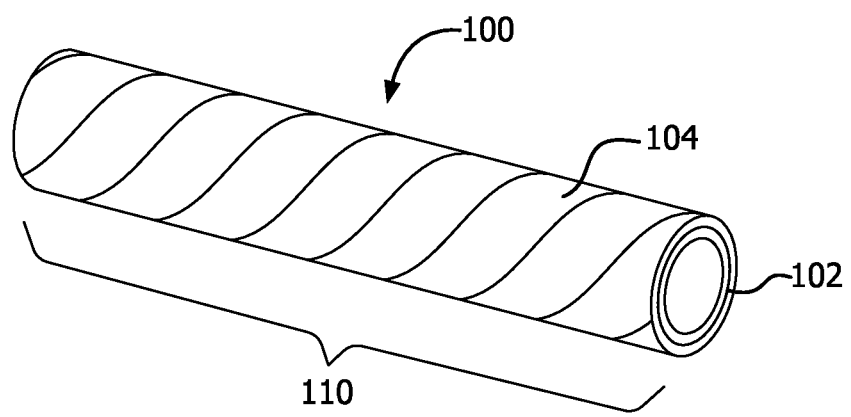
Figure 1C:
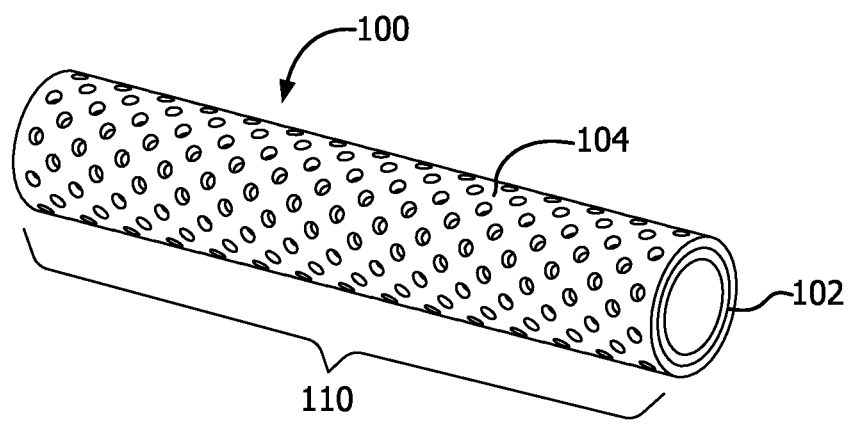

FIGS. 1A-1C describe perspective views of various example length extensible implantable devices 100 comprising a porous tubular member 102 and a longitudinal constraining member 104. Length extensible implantable device 100 can be implanted in the body of a patient either alone or in combination with one or more other components. For example, length extensible implantable device 100 can be combined with a suitable stent, forming a stent-graft. Further, length extensible implant 100 can be combined with other grafts and/or stent-grafts. In other embodiments, the length extensible graft 100 may be provided with a stent (or stent graft) on only one end or alternatively on more than one end or even each end of the length extensible graft 100. A stent graft is considered to be a stent provided with a graft covering all or a portion of the inner or outer surfaces of the stent or both the inner and outer surfaces of the stent. Devices with more than two ends are also contemplated, such as bifurcated devices. Any combination of length extensible implantable device 100 with any suitable medical device is within the scope of the present disclosure.

In various embodiments, porous tubular member 102 comprises a compressible, porous polymeric material, preferably an open celled material. For example, member 102 can comprise a porous expanded polymer, including expanded polytetrafluoroethylene ("ePTFE"), expanded modified PTFE (e.g. coated materials as described further below), expanded copolymers of PTFE, nylons, polycarbonates, polyethylenes, polypropylenes, polyurethanes and the like. These materials may also include materials having a porous fibrillated microstructure. It is also appreciated that these types of materials may be provided with coatings such as elastomeric coatings and coatings including therapeutic agents (e.g., heparin). Coatings may be provided as surface coatings or alternatively may partially or entirely impregnate the porous materials. Any suitable compressible porous polymer material is within the scope of the present disclosure.

Porous tubular member 102 can, for example, comprise an ePTFE construct. In various embodiments, porous tubular member 102 comprises a longitudinally extruded and longitudinally expanded ePTFE tube, such as the tubes described in U.S. Pat. Nos. 3,953,566 and 4,187,390. In other embodiments, polymeric tubular member 102 comprises a wrapped ePTFE film tube. For example, member 102 can comprises a tube made from an ePTFE film that has been cigarette wrapped on the surface of a mandrel or, alternatively, has been helically wrapped on the surface of a mandrel. Such ePTFE films of this type can be made generally as taught by U.S. Pat. Nos. 3,953,566 and 4,187,390. Likewise, conventional longitudinally extruded and expanded ePTFE tubes may be usefully reinforced with an external wrap of ePTFE film, typically, a helical wrap. However, any suitable porous ePTFE tubular member is within the scope of the present disclosure.

In various embodiments, porous tubular member 102 comprises an ePTFE tube having a multiplicity of fibrils which in turn can be connected to a multiplicity of nodes. The microstructure of porous tubular member 102 can comprise a multiplicity of fibrils having a mean fibril length. Mean fibril length can be determined, for example, by examining a photomicrograph of the surface of porous tubular member 102 and by taking the mean of ten measurements made in the predominant direction of the fibrils between nodes connected by fibrils. First, a photomicrograph is made of a representative region of the sample surface, of adequate magnification to show at least five sequential fibrils within the length of the photomicrograph. A series of five measurements are taken along a straight line drawn across the surface of the photomicrograph in the predominant direction of the fibrils followed by a second series of five measurements made along a second line drawn parallel to the first. A measurement constitutes the distance between adjacent nodes connected by at least one fibril. The ten measurements obtained by this method are meant to obtain the mean fibril length of the region.

For example, as illustrated in FIGS. 2A and 2B, porous tubular member 102 can comprise a microstructure of nodes 212, 222 interconnected by fibrils 214, 224.

In various embodiments, in the longitudinally uncompressed configuration, porous tubular member 102 can comprise a multiplicity of straight or unbent fibrils 214. Similarly, visual observation of a magnified longitudinal cross section of porous tubular member 102 indicates that a majority of the fibrils straight or unbent.

For example, after longitudinal compression, portion 110 of porous tubular member 102 comprises a multiplicity of bent fibrils 224. Similarly, visual observation of a magnified longitudinal cross section of portion 110 can indicate that a majority of the fibrils 224 connected to nodes 222 are relatively straight or unbent.

In various embodiments, at least a portion of porous tubular member 102 is held in a longitudinally compressed configuration by longitudinal constraining member 104. As illustrated in FIGS. 1A-1C, in such configurations, longitudinal constraining member 104 can surround a portion 110 of an abluminal surface of porous tubular member 102 and maintain portion 110 in the longitudinally compressed configuration. In various embodiments, portion 110 is the entire length of porous tubular member 102.

In various embodiments, portion 110 of porous tubular member 102, when compressed to the laterally compressed configuration, comprises a multiplicity of bent fibrils. In such embodiments, the mean fibril length in portion 110 is shorter than the mean fibril length of porous tubular member 102 in the initial, longitudinally uncompressed configuration. Further, visual observation of a magnified surface of portion 110 can indicate that a majority of the fibrils are relatively non-parallel and bent in relation to the longitudinal axis of the tubular member.

Longitudinal constraining member 104 can be capable of rupturing when force is applied in a particular direction. For example, in configurations in which a portion 110 of porous tubular member 102 is held in the longitudinal compressed configuration, applying tension to one or both ends of porous tubular member can cause longitudinal constraining member 104 to rupture. Rupture of longitudinal constraining member 104 can permit portion 110 to extend from the longitudinally compressed configuration to a less compressed configuration having fibrils that are less bent.

In other embodiments, longitudinal constraining member 104 can be ruptured by applying a radial force. For example, a balloon can be used to apply radial force to porous tubular member 102, rupturing longitudinal constraining member 104 and permitting extension of portion 110 to a lesser compressed configuration having fibrils that are less bent.

With reference to FIGS. 1A-1C, in various embodiments, longitudinal constraining member 104 can comprise a variety of different tubular forms. For example, longitudinal constraining member 104 can comprise an ePTFE film (e.g., a porous ePTFE film). In various embodiments, longitudinal constraining member 104 comprises an ePTFE film having a multiplicity of nodes connected by fibrils, such as those taught by U.S. Pat. Nos. 3,953,566, 4, 187,390, and 5,814, 405. However, any film suitable of constraining portion 110 of porous tubular member 102 in a longitudinally compressed configuration is within the scope of the present disclosure.

FIG. 1A illustrates a film wrapped around the surface of porous tubular member 102 at a low angle in relation to a longitudinal axis of the porous tubular member. For example, the film can be wrapped between about 0° and 45° relative to the longitudinal axis of porous tubular member 102.

In various embodiments, as illustrated in FIG. 1B, longitudinal constraining member 104 can comprise a film wrapped around the surface of porous tubular member 102 at a higher angle in relation to the longitudinal axis of the porous tubular member. For example, the film can be wrapped between about 45° and 90° relative to the longitudinal axis of porous tubular member 102.

In yet other embodiments, longitudinal constraining member 104 can comprise a tubular member capable of rupturing upon the application of a sufficiently large force. Such a tubular member can comprise a tubular wall having a multiplicity of slits, holes, and/or perforations that facilitate rupturing. As illustrated in FIG. 1C, longitudinal constraining member 104 can comprise, for example, a perforated tube. Although described in relation to particular examples and embodiments, any tubular member capable of maintaining porous tubular member 102 in a longitudinally compressed configuration and rupturing upon application of sufficient force is within the scope of the present disclosure.

Figure 3:
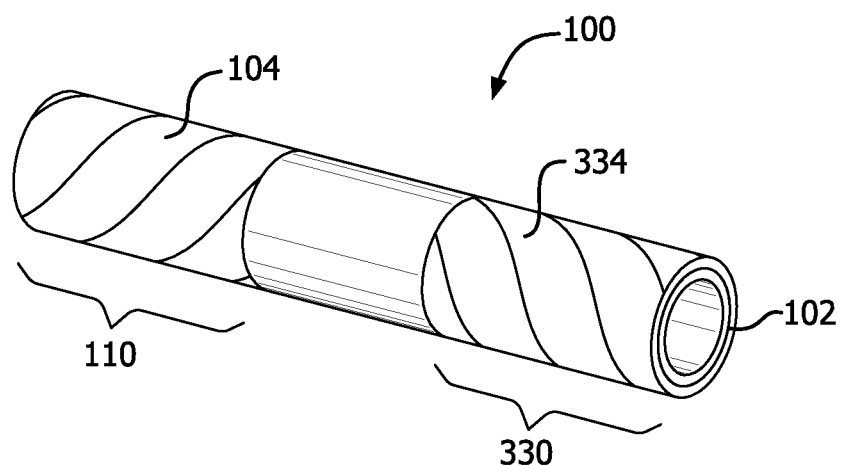
FIG. 3 is a perspective view of a length extensible implantable device in accordance with the present disclosure.

As illustrated in the perspective view of FIG. 3, implantable device 100 can comprise a first longitudinal constraining member 104 and a second longitudinal constraining member 334. For example, first longitudinal constraining member 104 can surround a first portion 110 of porous tubular member 102, and second longitudinal constraining member 334 can surround a second portion 330 of porous tubular member 102.

Figure 4:
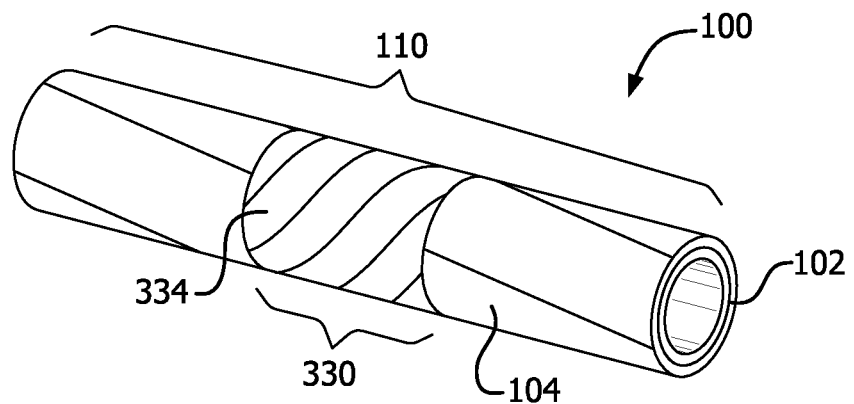
FIG. 4 is a perspective view of another length extensible implantable device in accordance with the present disclosure.

In various embodiments, first portion 110 and second portion 330 can comprise at least a part of the same portion, such that second longitudinal constraining member 334 surrounds first longitudinal constraining member 104. For example, the perspective view of FIG. 4 illustrates second longitudinal constraining member 334 surrounding second portion 330 and a part of first portion 110. Any configuration of first and second longitudinal constraining members, including partial or complete overlap of the two constraining members, is within the scope of the present disclosure. Further, the use of any number of longitudinal constraining members is within the scope of the present disclosure.

First longitudinal constraining member 104 and/or second longitudinal constraining member 334 can optionally be secured to porous tubular member 102, for example, to maintain the longitudinal constraining members in a desired orientation and position relative to porous tubular member 102. For example, first longitudinal constraining member 104 and/or second longitudinal constraining member 334 can be secured to porous tubular member 102 by applying an adhesive to a segment of an abluminal surface of porous tubular member 102 and/or the inner surface of the longitudinal constraining members. In various embodiments, a thermoplastic polymer adhesive, including a tetrafluoroethylene and perfluoromethyl vinyl ether copolymer, such as those described in U.S. Pat. No. 7,462,675, can be used. In other embodiments, a fluoroelastomer adhesive, such as a FEP, can be used. Any means capable of securing first longitudinal constraining member 104 and/or second longitudinal constraining member 334 to first porous tubular member 102 is within the scope of the present disclosure.

A method for making a length extensible implantable device of the present disclosure is described as follows. A porous tubular member in a longitudinally uncompressed configuration is obtained and fitted coaxially over a mandrel having an outside diameter the same as or slightly larger than the inside diameter of the porous tubular member. The tubular member is longitudinally compressed by a compressive force so that the length of the tube is reduced to a desired length. A longitudinal constraining member is placed over at least a portion of the porous tubular member to maintain the portion of the member in the longitudinally compressed configuration. The longitudinal constraining member can optionally be secured to the porous tubular member. The compressive force on the porous tubular member is released, and the longitudinally compressed porous tubular member is removed from the mandrel.

Figure 5A:
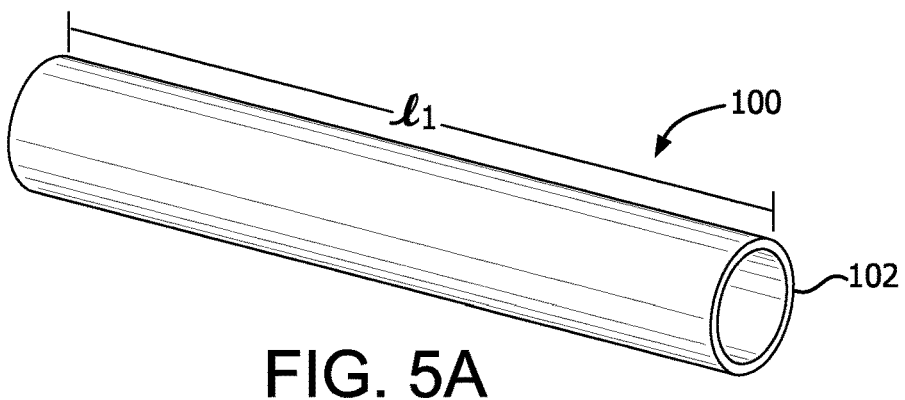
FIGS. 5A-5D are perspective views of a length extensible implantable device in various stages.

FIGS. 5A-5D illustrate a porous tubular member in various stages of a method for forming the porous tubular member into a length extensible implantable device. For example, FIG. 5A illustrates porous tubular member 102 in an initial, longitudinally uncompressed configuration. In the longitudinally uncompressed configuration, porous tubular member 102 can comprise a length l1.

Figure 5B:
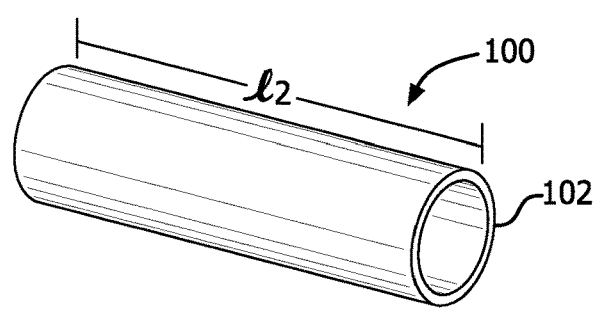

FIG. 5B illustrates porous tubular member 102 after a compressive force is applied. As the compressive force is applied, porous tubular member 102 is compressed from the initial, longitudinally uncompressed configuration to the longitudinally compressed configuration. In the longitudinally compressed configuration, porous tubular member 102 has a length l2, which is shorter than l1. In various embodiments, porous tubular member 102 is biased such that, upon release of the compressive force, it will at extend from l2 at least partially back to l1.

In various embodiments, l2 can comprise a length that is between about 50% and 75% of l1, such that compression from l1 to l2 reduces the length of porous tubular member 102 to between 50% and 75% of its uncompressed length. In other embodiments, l2 can comprise a length that is between about 25% and 50% of l1. In yet other embodiments, l2 can comprise a length that is between about 5% and 25% of l1. Any relationship between l2 and l1 is within the scope of the present disclosure.

Figure 5C:
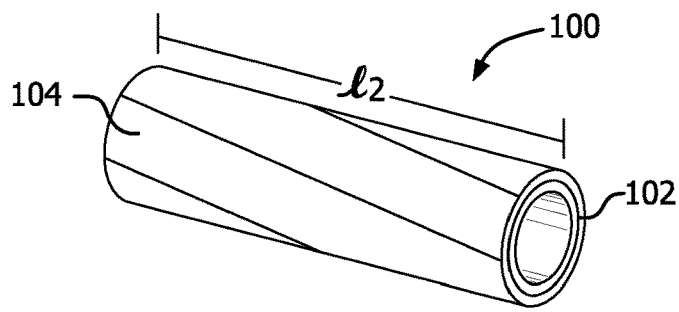

After porous tubular member 102 is compressed to a desired length l2, at least one longitudinal constraining member 104 is applied around the abluminal surface of porous tubular member 102 to maintain at least a portion 110 of porous tubular member 102 in the longitudinally compressed configuration. For example, FIG. 5C illustrates porous tubular member 102 covered by longitudinal constraining member 104. In various embodiments, and as illustrated in FIG. 5C, portion 110 covered by longitudinal constraining member 104 can comprise the entire length (l2) of porous tubular member 102. In other embodiments, portion 110 is less than the entire length of porous tubular members.

In various embodiments, longitudinal constraining member 104 comprises a film. In such embodiments, the film is wrapped around portion 110 of porous tubular member 102 in the longitudinally compressed configuration. As previously discussed, the film can be wrapped at a relatively low (about 0° to 45°) or a relatively high (about 45° to 90°) wrap angle relative to a longitudinal axis of porous tubular member 102. The film can also be wrapped at multiple angles, such as embodiments in which multiple layers of film are wrapped in multiple directions along the abluminal surface of porous tubular member 102.

In other embodiments, longitudinal constraining member 104 comprises a tubular element, such as a perforated tube. In such configurations, the tubular element is fitted along the surface of portion 110 of porous tubular member 102 in the longitudinally compressed configuration.

Longitudinal constraining member 104 can optionally be secured to porous tubular member 102. For example, an adhesive can be applied to the abluminal surface of porous tubular member 102. In other examples, an adhesive can be applied to the inner surface of longitudinal constraining member 104. However, as mentioned above, any manner of securing a longitudinal constraining member to a porous tubular member is within the scope of the present disclosure.

After portion 110 of porous tubular member 102 has been secured in the longitudinally compressed configuration by at least one longitudinal constraining member 104, the compressive force used to shorten porous tubular member 102 from l1 to l2 can be relieved while longitudinal constraining member 104 maintains portion 110 in a compressed configuration, forming length extensible implantable device 100. If portion 110 comprises less than the entire length of porous tubular member 102, upon release of the compressive force, the segment of porous tubular member 102 not constrained can expand to its original length, leaving only portion 110 in the longitudinally compressed configuration. In embodiments in which the entirety length of porous tubular member 102 is covered by longitudinal constraining member 104 (in other words, where portion 110 is equal to l2), all of porous tubular member 102 remains in the longitudinally compressed configuration.

In various embodiments, a second porous tubular member can be positioned around portion 110, portion 330, and or all of porous tubular member 102. In such configurations, longitudinal constraining members 104 and/or 334 are sandwiched between porous tubular member 102 and a second porous tubular member, such that longitudinal constraining members 110 and/or 330 cannot be seen when visually examining the outer surface of length extensible implantable device 100.

Figure 5D:
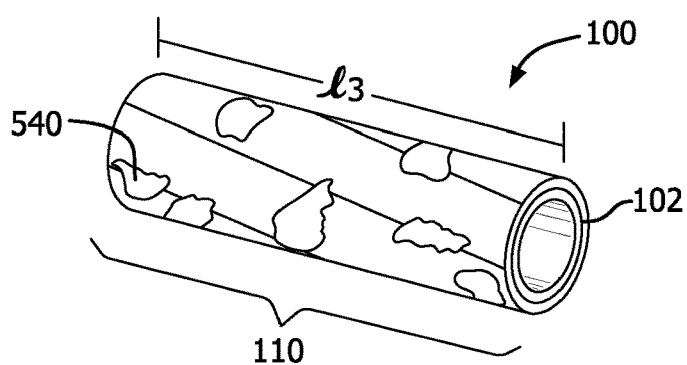

After length extensible implantable device 100 is formed, it can be adjusted and configured for use within the body of a patient. In various embodiments, as illustrated in FIG. 5D, the length of length extensible implantable device 100 can be expanded to a length l3, which is greater than l2 and less than or equal to the length of porous tubular member 102 in the initial, laterally uncompressed configuration (having a length of l1). In various embodiments, as force is applied to porous tubular member 102, longitudinal constraining member 104 can rupture or tear, forming one or more ruptures 540. Once sufficient force is applied, porous tubular member 102 can continue expanding until it has expanded back to l1.

In various embodiments, portion 110 of porous tubular member 102 can be extended from the longitudinally compressed configuration to a longer length (such as l3) by applying a force parallel to the longitudinal axis of porous tubular member 102. In other embodiments, portion 110 of porous tubular member 102 can be extended from the longitudinally compressed configuration to l3 by applying a radial force to portion 110.

For example, a treatment provider can determine a desired length of length extensible implantable device 100 before implanting the device into the vasculature of a patient. In other cases, the treatment provider can determine the desired length of length extensible implantable device 100 during the course of implanting the device into the vasculature and delivering the device to a treatment area of the patient.

Several characteristics and advantages have been set forth in the preceding description, including various alternatives together with details of the structure and function of the devices and methods. The disclosure is intended as illustrative only and as such is not intended to be exhaustive or limiting. It will be evident to those skilled in the art that various modifications may be made, especially in matters of structure, materials, elements, components, shapes, sizes, and arrangements of parts including combinations within the principles described herein, to the full extent indicated by the broad, general meaning of the terms in which the appended claims are expressed. To the extent that these various modifications depart from the spirit and scope of the appended claims, they are intended to be encompassed therein.

What is claimed is:

1. An implantable device having an extendible length, the implantable device comprising:
   a porous member comprising a microstructure including a multiplicity of fibrils,
   wherein the porous member comprises a longitudinally uncompressed configuration and a longitudinally compressed configuration, wherein a mean fibril length in the longitudinally uncompressed configuration is greater than a mean fibril length in the longitudinally compressed configuration and a compressed length of the porous member in the longitudinally compressed configuration is approximately between 50% and 75% of an extended length of the porous member in the longitudinally uncompressed configuration; and
   a first longitudinal constraining member secured to the porous member along a length of the porous member by an adhesive, the first longitudinal constraining member maintaining at least a portion of an abluminal surface of the porous member in the longitudinally compressed configuration with a constraining force, the first longitudinal constraining member being configured to release the constraining force upon application of a radial force within a lumen of the porous member while patency of the lumen of the porous member is maintained and upon release of the constraining force, at least a segment of the porous tubular member is configured to expand to and maintain the extended length relative to a longitudinal axis of the porous member in the absence of the radial force.

2. The implantable device of claim 1, further comprising a second porous member covering the longitudinal constraining member.

3. The implantable device of claim 1, wherein the porous member is a tubular member.

4. The implantable device of claim 1, wherein the first longitudinal constraining member comprises a porous ePTFE film.

5. The implantable device of claim 4, wherein the porous ePTFE film is wrapped over the at least a portion of the abluminal surface of the porous member at an angle relative to the longitudinal axis of the porous member.

6. The implantable device of claim 1, wherein the first longitudinal constraining member covers more than one portion of the abluminal surface of the porous member.

7. The implantable device of claim 1, wherein the first longitudinal constraining member covers the entire abluminal surface of the porous member.

8. The implantable device of claim 1, wherein the microstructure of the porous member includes a multiplicity of nodes.

9. The implantable device of claim 1, further comprising at least a second longitudinal constraining member.

10. The implantable device of claim 9, wherein the first and second longitudinal constraining members cover different portions of the abluminal surface of the porous member.

11. The implantable device of claim 1, wherein at least a segment of the first longitudinal constraining member is ruptured by applying a longitudinal force to the longitudinal constraining member and the porous member, wherein upon rupturing, at least a portion of the porous member covered by the segment of first longitudinal constraining member longitudinally extends.

12. The implantable device of claim 1, wherein the porous member is a porous ePTFE member, and further wherein the longitudinally compressed configuration of the porous ePTFE member comprises a longitudinally compressed portion including bent fibrils.

13. The implantable device according to claim 12 wherein the porous ePTFE member is a tubular member.

14. The implantable device of claim 13, wherein the first longitudinal constraining member is a perforated sleeve.

15. The implantable device of claim 13, wherein the first longitudinal constraining member comprises a film wrapped around at least a portion of the abluminal surface of the porous member at an angle relative to a longitudinal axis of the porous member.

16. The implantable device of claim 12, wherein the constraining member comprises a porous ePTFE film.

17. The implantable device of claim 16, wherein the porous ePTFE film has a plurality of nodes interconnected by fibrils, wherein the nodes are generally aligned so as to be substantially parallel to each other.

18. The implantable device of claim 12, wherein upon application of an elongating force to the porous ePTFE member, the first longitudinal constraining member ruptures and permits elongation of the longitudinally compressed portion from a first length to a second length, wherein upon release of the elongating force, the elongated compressed portion recovers to a third length shorter than the second length and longer than the first length.

19. The implantable device of claim 12, further comprising a stent having an inner surface and an outer surface, the porous member and longitudinal constraining member covering at least a portion of at least one of the inner and outer surfaces of the stent.

20. The implantable device of claim 12, wherein the porous ePTFE member comprises the longitudinally compressed portion and a longitudinally uncompressed portion.

21. The implantable device of claim 20, wherein a mean fibril length in the longitudinally uncompressed portion is greater than a mean fibril length in the longitudinally compressed portion.

22. An implantable device having an extendible length, the implantable device comprising:
a porous member comprising a microstructure including a multiplicity of fibrils,
wherein the porous member comprises a longitudinally uncompressed configuration and a longitudinally compressed configuration, wherein a mean fibril length in the longitudinally uncompressed configuration is greater than a mean fibril length in the longitudinally compressed configuration and a compressed length of the porous member in the longitudinally compressed configuration is approximately between 50% and 75% of an extended length of the porous member in the longitudinally uncompressed configuration; and
a first longitudinal constraining member secured to the porous member along a length of the porous member by an adhesive, the first longitudinal constraining member maintaining at least a portion of an abluminal surface of the porous member in the longitudinally compressed configuration with a constraining force, the first longitudinal constraining member being configured to release the constraining force upon application of a radial force within a lumen of the porous member while patency of the lumen is maintained and upon release of the constraining force, at least a segment of the porous tubular member is configured to expand to and maintain the extended length relative to a longitudinal axis of the porous member in the absence of the radial force.

23. An implantable device having an extendible length, the implantable device comprising:
a porous member comprising a microstructure including a multiplicity of fibrils,
wherein the porous member comprises a longitudinally uncompressed configuration and a longitudinally compressed configuration, wherein a mean fibril length in the longitudinally uncompressed configuration is greater than a mean fibril length in the longitudinally compressed configuration and a compressed length of the porous member in the longitudinally compressed configuration is approximately between 50% and 75% of an extended length of the porous member in the longitudinally uncompressed configuration; and
a first longitudinal constraining member secured to the porous member along a length of the porous member by an adhesive, the first longitudinal constraining member maintaining at least a portion of an abluminal surface of the porous member in the longitudinally compressed configuration with a constraining force, the first longitudinal constraining member being configured to release the constraining force upon application of a radial force within a lumen of the implantable device to permit the porous member to extend from the longitudinally compressed configuration to expand and maintain the extended length relative to a longitudinal axis of the porous member in the absence of the radial force.

* * * * *